(12) United States Patent
Harrington

(10) Patent No.: US 8,887,729 B2
(45) Date of Patent: Nov. 18, 2014

(54) TRACHEOSTOMY TUBE ASSEMBLIES HAVING SPHERICAL BEARING ELEMENTS

(75) Inventor: Roger Harrington, Athlone (IE)

(73) Assignee: Covidien LP, Mansfield, MA (US)

(*) Notice: Subject to any disclaimer, the term of this patent is extended or adjusted under 35 U.S.C. 154(b) by 798 days.

(21) Appl. No.: 13/076,859

(22) Filed: Mar. 31, 2011

(65) Prior Publication Data

US 2012/0247478 A1 Oct. 4, 2012

(51) Int. Cl.
*A61M 16/00* (2006.01)
*A61M 16/08* (2006.01)
*A61M 16/04* (2006.01)

(52) U.S. Cl.
CPC ....... *A61M 16/0465* (2013.01); *A61M 16/0816* (2013.01); *A61M 16/0479* (2014.02); *A61M 16/0825* (2014.02); *A61M 16/0497* (2013.01); *A61M 16/0434* (2013.01)
USPC .................................................. 128/207.14

(58) Field of Classification Search
CPC ..................... A61M 16/0465; A61M 16/0434; A61M 16/0666; A61M 16/0488
USPC ............. 128/200.26, 200.27, 207.14, 207.15, 128/207.17, 205.22; 285/138.1, 145.3, 261, 285/264, 265; 403/113, 114, 124
See application file for complete search history.

(56) References Cited

U.S. PATENT DOCUMENTS

| | | | |
|---|---|---|---|
| 1,478,066 A * | 12/1923 | Sampson | 174/61 |
| 1,742,419 A * | 1/1930 | Selah | 285/264 |
| 3,973,569 A | 8/1976 | Sheridan et al. | |
| 4,033,353 A | 7/1977 | La Rosa | |
| 4,340,046 A | 7/1982 | Cox | |
| 4,457,188 A * | 7/1984 | Hauser | 74/473.36 |
| 5,259,376 A * | 11/1993 | Bales | 128/207.17 |
| 5,361,754 A | 11/1994 | Stuart | |
| 5,435,306 A | 7/1995 | Stuart | |
| 5,778,877 A | 7/1998 | Stuart | |
| 5,819,734 A | 10/1998 | Deily et al. | |
| 6,053,167 A | 4/2000 | Waldeck | |
| 6,284,179 B1 | 9/2001 | Deily et al. | |
| 2005/0166924 A1 | 8/2005 | Thomas et al. | |
| 2007/0083262 A1 | 4/2007 | Matlock | |
| 2007/0255258 A1 | 11/2007 | Matlock et al. | |
| 2008/0149107 A1 | 6/2008 | Byatt | |
| 2009/0229614 A1 | 9/2009 | Bateman | |
| 2009/0308397 A1 | 12/2009 | Neame | |
| 2010/0319705 A1 | 12/2010 | Thomas et al. | |

OTHER PUBLICATIONS

Teleflex Medical: Rusch; 2009 Teleflex Incorporation; 9 pgs.
Tracoe Medical GmbH—Products-Vario; Apr. 1, 2010; 22 pgs.

* cited by examiner

*Primary Examiner* — Melanie Hand
*Assistant Examiner* — Ned T Heffner
(74) *Attorney, Agent, or Firm* — Fletcher Yoder PC

(57) ABSTRACT

Various embodiments of tracheostomy tube assemblies including a first subassembly and a flange subassembly are provided. The first subassembly includes a connector and a first spherical bearing element coupled to a first end of the connector. The first spherical bearing element includes at least two protrusions radially offset about a circumference of the first spherical bearing element. The flange subassembly includes an outer spherical bearing element having recesses for receiving the at least two protrusions and being adapted to encapsulate the first spherical bearing element.

18 Claims, 5 Drawing Sheets

TRACHEOSTOMY TUBE ASSEMBLIES HAVING SPHERICAL BEARING ELEMENTS

BACKGROUND

The present disclosure relates generally to medical devices and, more particularly, to airway devices, such as tracheostomy tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes, may be used to control the flow of air and medicaments into or out of a patient's airway. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

More specifically, tracheal tubes may be used to control the flow of air or other gases through a patient's trachea. Such tracheal tubes may include endotracheal tubes or tracheostomy tubes. While patients may be intubated using endotracheal tubes during emergencies or shorter hospital stays, tracheostomy tubes are typically used for prolonged ventilation, as the use of a tracheostomy tube may be more comfortable for a patient.

A typical tracheostomy tube is generally inserted into the trachea via a surgical incision in the neck. After insertion of the tube into the trachea, a portion of the tracheostomy tube remains outside the patient. This portion extends outwards from the neck and may connect the tracheostomy tube to a ventilator or other medical device. Generally, this exterior portion of the tube is held in place by a flange that rests on the patient's neck and is further secured by straps to the patient. The inserted portion of the tracheostomy tube is generally mechanically coupled to the flange, typically by molding, adhesives, bonding, or mechanical means such as a snap or screw mechanism on the underside of the flange, which rests on the patient's neck. As such, the mechanical connection point often inhibits freedom of movement of the flange with respect to the inserted portion such that during prolonged intubation periods, patient movement may not be accommodated by the tube and flange design.

In response to this drawback, many current tracheostomy tubes have been designed to facilitate movement between the tube and the flange in a single plane (e.g., allowing upward and downward motion), providing some additional comfort for the patient. Unfortunately, these tracheostomy tubes may still translate the forces associated with patient movement to the cannula located within the trachea, thereby exerting pressure on the tracheal wall, which may lead to patient discomfort. That is, because the exterior portion of the tracheostomy tube is connected to the inserted portion, when the exterior portion of the tube is shifted or moved, these movements may be translated to the interior potion of the tube. These movements may cause some discomfort for the patient if the tracheostomy tube shifts position within the trachea. Accordingly, there exists a need for tracheostomy tubes that reduce patient discomfort without translating patient movement to the interior portion of the inserted tracheostomy tube.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
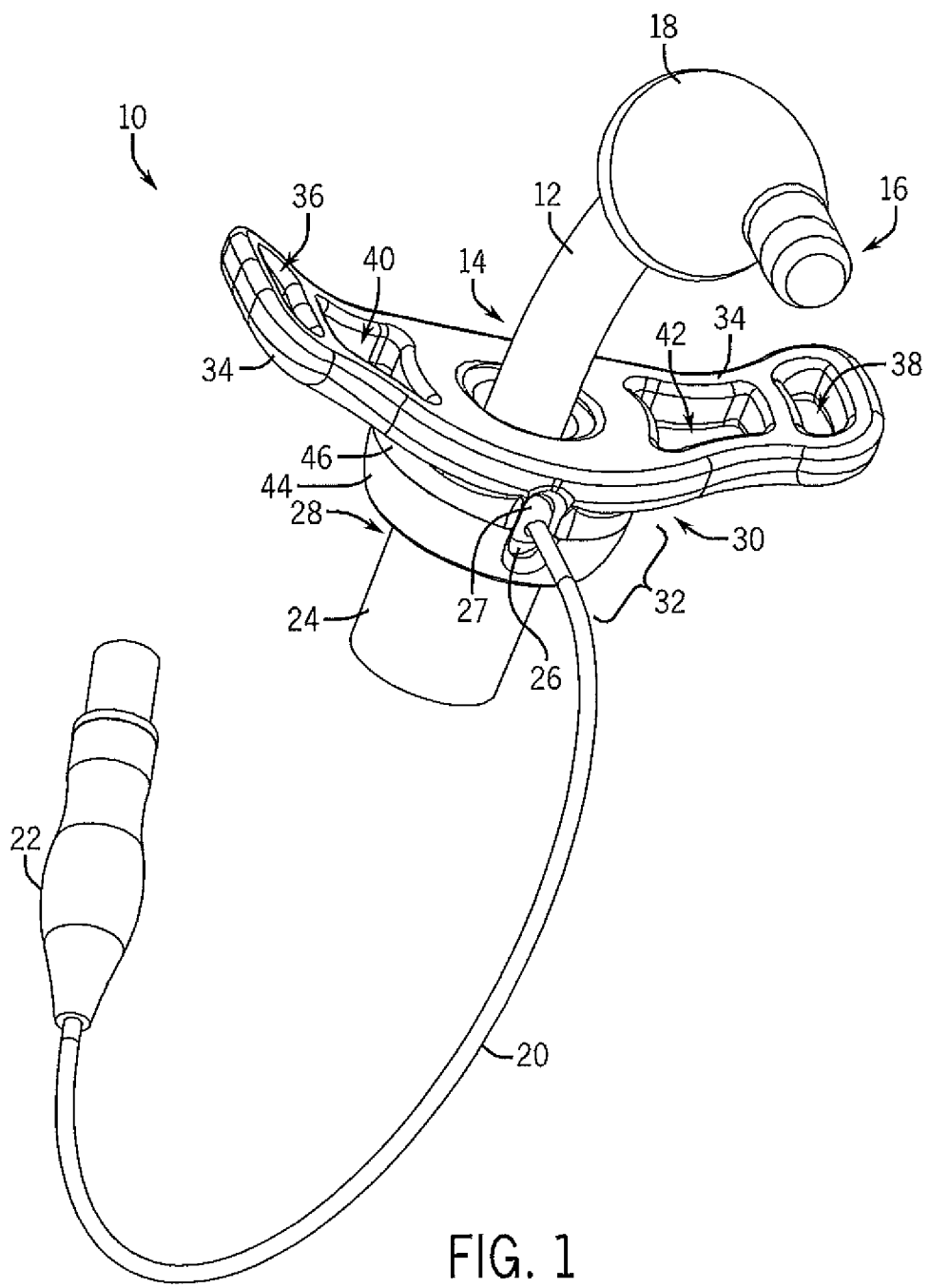
FIG. 1 is a perspective view of a tracheostomy tube assembly including an inner spherical bearing element having protrusions and an outer spherical bearing element having recesses according to an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, provided herein are tracheostomy tube assemblies including features that enable flange movement in more than one plane of motion with respect to a cannula while reducing or eliminating the translation of such movement to the cannula when disposed in a patient's trachea. For example, certain embodiments provide for the motion of the flange in both a horizontal plane (e.g., between leftward and rightward positions) and a vertical plane (e.g., between upward and downward positions). As such, these embodiments may offer advantages over traditional designs that limit flange movement to one plane of motion because as the patient's head is tilted between positions (e.g., from an upward and rightward position to a downward and leftward position), the cannula may remain aligned within the patient's trachea. That is, presently contemplated embodiments may provide for movement of the external flange coupled to the patient's neck while reducing or preventing the likelihood of cannula rotation within the patient's trachea. By providing this additional freedom of movement of the flange with respect to the cannula without substantial displacement of the cannula, current embodiments may increase patient comfort. For example, in presently disclosed designs, the movement of the flange member, which rests against the patient's neck, may more closely follow patient movement as compared to traditional designs.

Turning now to the features of the disclosed tracheostomy tube assemblies that provide this freedom of movement, certain embodiments of the presently disclosed tube assemblies may include a first subassembly having a lower cannula, an upper connector, and an inner spherical bearing element disposed between the lower cannula and the upper connector. This inner spherical bearing element may include protrusions radially disposed about its circumference and dimensioned such that the protrusions fit within recesses disposed in an outer spherical bearing element that encircles the inner spherical bearing element. As such, when assembled, the protrusions of the inner spherical bearing element are adapted to move within the recesses of the outer spherical bearing element. For example, in one embodiment, the protrusions may be spherically shaped and the recesses may be hemispherical, thus enabling movement between the spherical bearing elements in both the horizontal and vertical planes. In some embodiments, the outer spherical bearing element may be partially or fully integrated into a flange assembly, and, therefore, the spherical bearing elements may enable movement of the flange assembly in at least two planes with respect to the first subassembly, which includes the cannula. Again, such physical features may enable the flange member to conform to the movement of the patient's neck during use without translating such movement to the cannula. That is, in certain embodiments, the tracheostomy tubes may include features that reduce the outside forces (e.g., those produced during movement of the patient's neck) that may be transferred to the inserted portion of the tube, which may cause discomfort if the tube shifts position and contacts the trachea.

In the embodiments illustrated herein, the inner spherical bearing element includes six spherical protrusions suitably sized to be retained within six hemispherical pathways of the outer bearing element. However, the illustrated embodiments are merely examples and are not intended to constrain or limit forms which the inner spherical bearing elements may take; other sizes, shapes, quantity of protrusions, and configurations are also within the scope of the disclosed inner spherical bearing elements. Still further, the illustrated outer spherical bearing element is formed from a boss member and a flange member, which each form a portion of each hemispherical pathway. However, in other embodiments, this assembly may be a single manufactured piece or may be formed from more than two elements. Here again, the shown embodiments of the outer spherical bearing element are merely examples that illustrate the enabled functionality, and the disclosed outer spherical bearing elements are meant to encompass a variety of other sizes, shapes, and forms.

The tracheostomy tube assemblies may be disposable rather than reusable and may be capable of conveying gas to and from the patient, such as during medical situations that necessitate prolonged ventilation. As such, the devices and techniques provided herein may enable maintaining a bidirectional gas flow between the patient and an external ventilation device. Accordingly, the tracheostomy tube assemblies provided herein may be adapted to be inserted into the trachea via a surgical incision in the neck such that after insertion of the tube into the trachea, a portion of tube remains outside the patient. This portion extends outwards from the neck and may connect the tracheostomy tube to a ventilator or other medical device. That is, the provided tracheostomy tube assemblies may be used in conjunction with auxiliary devices, such as airway accessories, ventilators, humidifiers, and so forth, which may cooperate with the tube assemblies to maintain airflow to and from the lungs of the patient. For example, the tracheal tubes may be coupled to an adapter or connector that is configured to couple the tracheostomy tube assemblies described herein to the desired auxiliary device.

Turning now to the drawings, FIG. 1 is a perspective view of an embodiment of a tracheostomy tube assembly 10. In the depicted embodiment, the tracheostomy tube assembly 10 includes an arcuate cannula 12 having a proximal end 14 and a distal end 16, which is generally sized and configured to be inserted into a patient's neck through a surgical incision for prolonged ventilation. When the tracheostomy tube assembly 10 is in use, the distal end 16 as well as the major portion of the length of the cannula 12 will reside within the trachea, with the proximal end 14 being generally flush with the anterior surface of the patient's neck.

In some embodiments, the cannula 12 may also feature a small lumen within the wall, terminating in a notch that may be used to fill a balloon type sealing cuff 18 at the patient insertion end. In some embodiments, the cuff 18 may be a urethane balloon bonded to the exterior of the cannula 12 such that the notch is encompassed. In these embodiments, the cuff 18 may be inflated within the patient's airway to provide an additional seal. The cuff 18 may be inflated via an inflation tube 20 coupled to the inflation lumen of the cannula 12 on one end and terminating in a cuff inflator valve assembly 22 on the other end. The cuff inflator valve assembly 22 may be coupled to a ventilator configured to deliver a gas, such as air, through the inflation lumen and into the cuff 18. The cuff 18, when inflated, will expand radially around the cannula 12 to seal the patient's airway. By using one or more cuffs 18 to seal the patient's airway, substances may flow only through the cannula 12, which may allow improved control over the type and amount of substances flowing into and out of the patient as compared to tube assemblies without one or more cuffs. It should be noted that the cuff 18 may be any suitable cuff, such as a tapered cuff, a non-tapered cuff, and so forth.

In some embodiments, the cannula 12 may also include a suction lumen (not shown in FIG. 1) that extends from a location on the proximal end 14 of the cannula 12 positioned outside the body when in use to a location around the cuff 18 inside the body. The suction lumen may terminate in a port through which secretions accumulated around the cuff may be aspirated. For example, a port may be located above the cuff 20 or one or more ports may be located anywhere along the length of the cannula 12 such that they aspirate secretions from the airway of the patient. Further, in some embodiments, an exterior suction tube may connect to the suction lumen for the removal of the suctioned fluids, for example, via a vacuum connected to the exterior suction tube.

In the illustrated embodiment, the tracheostomy tube assembly 10 also includes an upper connector 24 that is substantially in line with the proximal end 14 of the cannula 12. The upper connector 24 may be adapted to directly or indirectly connect the tracheostomy tube assembly 10 to any suitable medical device. For example, in dual cannula tracheostomy tubes, the upper connector 24 may serve as an insertion point for a disposable cannula lining or may be suitably sized and shaped to connect the tracheostomy tube assembly 10 via medical tubing, suitable connectors, or other devices to a mechanical ventilator. For further example, the upper connector 24 may directly couple to a ventilator or other suitable device to maintain an exchange of fluid (e.g., air) between the patient and the support device during periods of intubation. In the illustrated embodiment, the upper connector 24 is coupled to an inner spherical bearing element 26 (only partially shown in FIG. 1) that retains the proximal end 14 of the cannula 12 therein. The inner spherical bearing element 26 includes two or more protrusions 27 radially disposed about a circumference of the inner spherical bearing element 26, as shown and described in more detail in FIGS. 2 and 6. In some embodiments, the cannula 12, the upper connector 24, and the inner spherical bearing element 26 may form a first subassembly 28. Features of the components of the first subassembly 28 will be discussed in more detail below.

In the assembled view illustrated in FIG. 1, the inner spherical bearing element 26 in encased within a flange assembly 30. The flange assembly 30 includes an outer spherical bearing element 32 and flanges 34. The flanges 34 are adapted to rest on the neck of the patient during use and feature openings 36 and 38 designed to accommodate attachment straps that may be utilized to secure the tracheostomy tube assembly 10 to the patient's neck. The flanges 34 also include apertures 40 and 42 for providing improved air flow to the stoma site when the flanges 34 rest against the patient's neck. In some embodiments, the flange assembly 30 may be made of a suitable flexible thermoplastic material. For example, in certain embodiments, the flange assembly 30 may be made of a soft PVC molding, which may provide for increased patient comfort when the flanges 34 rest against the patient's neck during use. However, in some embodiments, during manufacturing, the flange assembly 30 may be first composed of a rigid thermoplastic material (e.g. polyvinyl chloride (PVC)) and then overmolded with a flexible thermoplastic material (e.g., PVC). Indeed, in still further embodiments, the flange assembly 30 may be formed in any desired way from any of a variety of suitable materials, as would be understood by one skilled in the art.

In the illustrated embodiment, the outer spherical bearing element 32 includes a boss member 44 and a base portion 46. Each of the boss member 44 and the base portion 46 includes a portion of each pathway that is configured to receive each of the protrusions located on the inner spherical bearing element 46. That is, the boss member 44 and the base portion 46 are configured to be assembled such that when properly aligned, pathways are provided that receive the protrusions 27 on the inner spherical bearing element 26. In this way, when assembled as shown in FIG. 1, the boss member 44 and the base portion 46 of the outer spherical bearing element 32 enclose the inner spherical bearing element 26, and features of the inner spherical bearing element 26 (i.e., the radially disposed protrusions) and features of the outer spherical bearing element 32 (i.e., the hemispherical pathways) interact to provide for motion of the flange assembly 30 with respect to the cannula 12 in both the vertical and horizontal planes. In particular, the protrusions of the inner spherical bearing element 26 are free to move within the hemispherical tracks of the outer spherical bearing element 32.

In the described way, embodiments of the presently disclosed tracheostomy tubes enable angular rotation of the inner spherical bearing element 26 in two orthogonal directions (i.e., horizontal and vertical) about the center point of the sphere defined by the inner bearing element. That is, structural features of embodiments of the presently disclosed tracheostomy tubes may enable the flange assembly 30 to rotate, slide, and otherwise move to accommodate outside forces, such as those generated by movement of the patient's neck. For example, if the patient exerts a force on the flange assembly 30 via neck movement, at least a portion of that force is translated into movement of the inner spherical bearing element 26 such that the portion of the cannula 12 disposed inside the patient's trachea does not experience the full force exerted on the flange member 30. As such, rotational movement of the cannula 12 may be reduced, which may result in enhanced patient comfort as compared to traditional tracheostomy assemblies in which movement of the flange often translates into movement of the cannula within the trachea.

Figure 2:
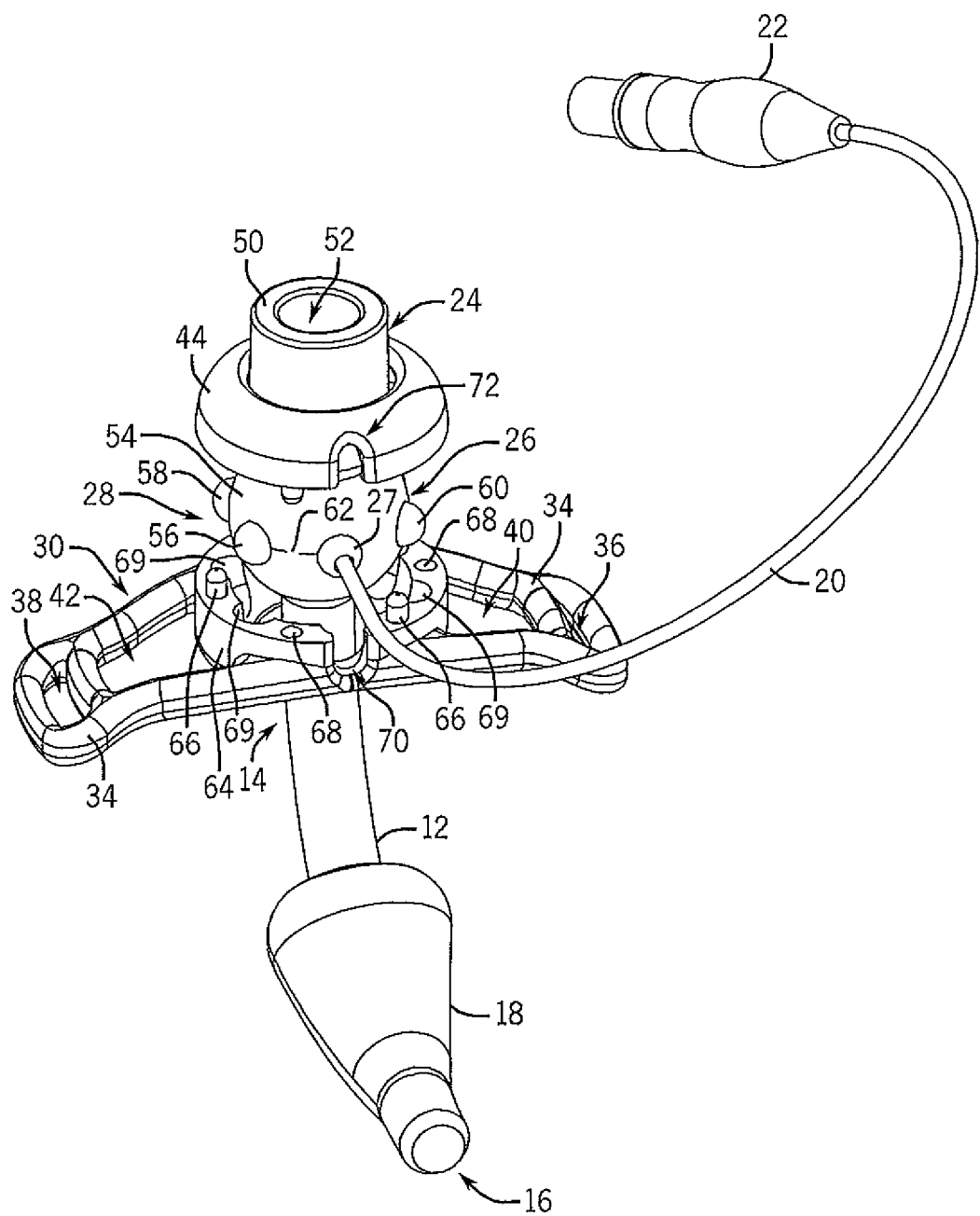
FIG. 2 is a partially exploded view of the embodiment of the tracheostomy tube assembly of FIG. 1.

Turning now to these structural features, FIG. 2 is a partially exploded view of embodiments of components of the tracheostomy tube assembly 10 of FIG. 1. In the illustrated view, the first subassembly 28 including the cannula 12, the inner spherical bearing element 26, and the upper connector 24 is shown in a preassembled configuration. As shown, the upper connector 24 includes a generally hollow, cylindrical body 50 having an aperture 52 extending therethrough. The aperture 52 is suitable for enabling a free flow of fluids, such as air, throughout the length of the first subassembly 28 when the upper connector 24 is assembled with the inner spherical bearing element 26 and the cannula 12 during use in a patient. Still further, the diameter of the cylindrical body 50 and the diameter of the aperture 52 of the upper connector 24 may be dimensioned to accommodate various sized connectors associated with suitable auxiliary equipment as desired for the given application.

The inner spherical bearing element 26 of the first subassembly 28 includes a generally spherical base 54 with six protrusions 27, 56, 58, and 60 (two others not shown in FIG. 2) radially disposed about the circumference of the spherical base 54. In other words, each protrusion is radially offset around the circumference of the spherical base 54 by an angular displacement 62. For example, in the illustrated embodiment, each of the six protrusions is radially displaced with respect to the next radial protrusion by approximately 60° such that each of the six protrusions is approximately equidistant from each adjacent protrusion. However, the illustrated embodiment is merely an example and is not meant to limit forms which the protrusions or the spherical base make take. In other embodiments, any suitable quantity of protrusions, spacing between protrusions, and so forth, may be implemented within the scope of presently disclosed embodiments. Further, the shape, size, and other features of the inner spherical bearing element 26 may be subject to considerable variations. For example, in some embodiments, the spherical base 54 may be generally circular instead of spherical, made of multiple pieces instead of being a single piece, and so forth.

As shown, the proximal end 14 of the cannula 12 is retained within the inner spherical bearing element 26 when assembled. As such, when assembled, a passageway, through which fluid may flow to and from a patient, is established between the distal portion 16 of the cannula 12, the inner spherical bearing element 26, and the upper connector 24. Additionally, a fluid passageway may be established between an external inflation device and the cuff 18 via inflation conduit 20 and assembly 22. This additional passageway enables an operator to inflate and deflate the cuff 18 as desired for the given medical application. As shown, the inflation conduit 20 that establishes this passageway is coupled to the inflation lumen disposed in the cannula 12 via an opening disposed in the protrusion 27 in the spherical body 54. In some embodiments, the relative movement of the inflation conduit 20 may be limited to a single plane such that the improved flange assembly still provides for the desired cuff inflation.

In the illustrated partially exploded view, the flange assembly 30 includes flanges 34, boss member 44, and an annular ring portion 64. In some embodiments, the boss member 44 and the annular ring portion 64 may form the outer spherical bearing element 32 that encircles the inner spherical bearing element 26. As such, the annular ring 64 includes features that facilitate an aligned coupling of the boss member 44 thereto. For example, the annular ring 64 includes protrusions 66 and apertures 68 that are configured to mate with corresponding apertures and protrusions disposed on an underside of the boss member 44 (not shown in FIG. 2). Still further, the annular ring 64 also includes recesses 69 that are configured to receive the protrusions 56, 58, and 60 of the inner spherical bearing element 26. In some embodiments, these recesses 69 may mate with matching recesses in the boss member 44 to form hemispherical pathways through which the protrusions may rotate during operation of the tube assembly 10.

Further, the flange assembly 30 may include features that enable coupling of the inflation line 20 and/or an evacuation line (not shown in FIG. 2) to lumens disposed in the cannula 12. For example, in the embodiment of FIG. 2, a notch 70 disposed in the annular ring 64 pairs with a notch 72 disposed in the boss member 44 to provide a track for protrusion 27 that couples to inflation line 20. As such, during operation, the flange member 30 may move about the protrusion 27 including the inflation line 20 without substantial translation of such movement to the cannula 12 disposed within the patient's trachea.

Figure 3:
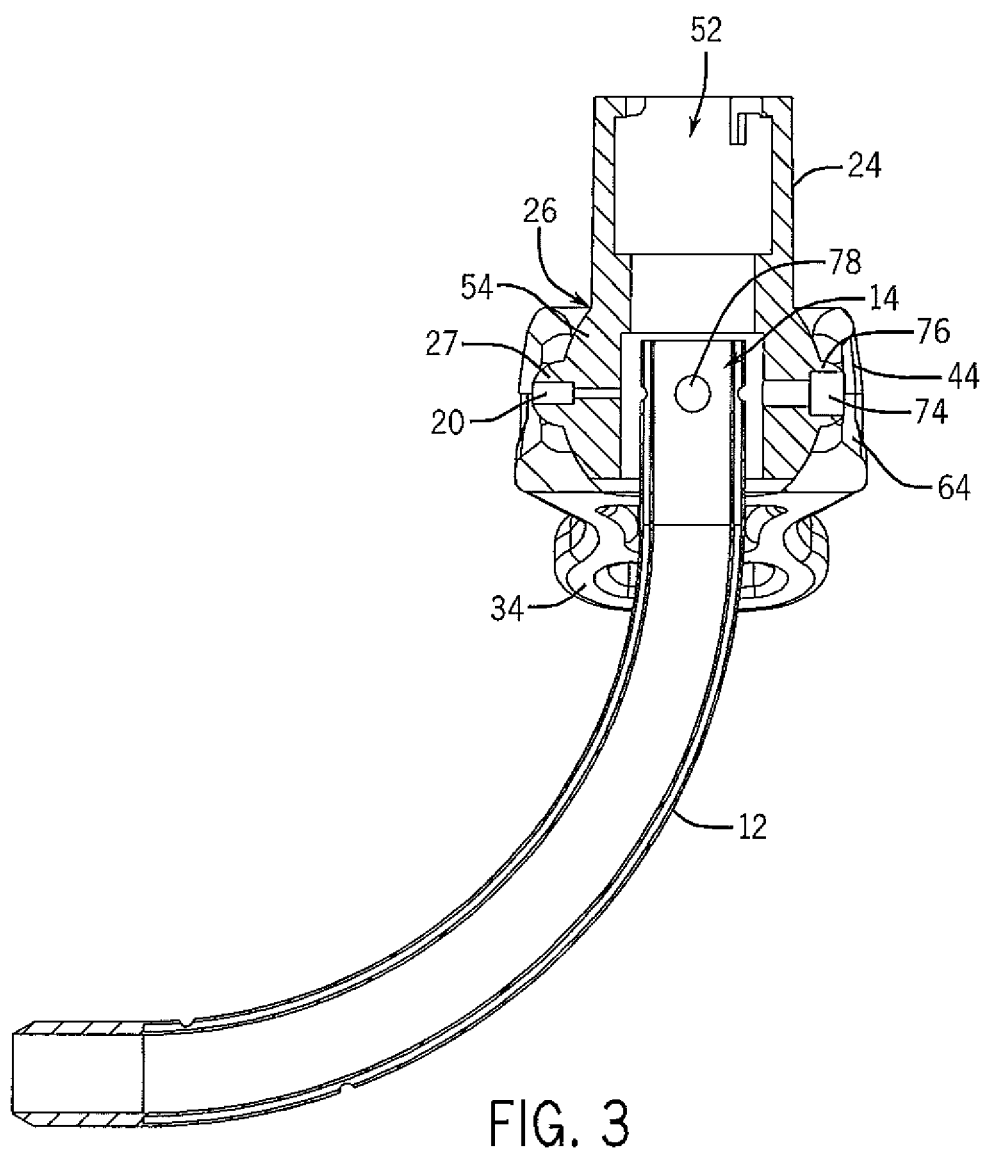
FIG. 3 is a sectional view of the tracheostomy tube assembly of FIG. 1 illustrating the inner spherical bearing element and outer spherical bearing element arrangement in more detail.

FIG. 3 illustrates a sectional view of the tracheostomy tube assembly 10 of FIGS. 1 and 2 showing these features in more detail. For example, as shown, in FIG. 3, the inflation line 20 couples to the cannula 12 via the spherical protrusion 27. Similarly, an evacuation line 74 couples to an evacuation lumen in the cannula 12 via a protrusion 76 disposed in the spherical body 54 of the inner spherical bearing element 26. As shown in FIG. 2 with respect to the inflation line, the protrusion 76 that houses the evacuation line 74 may be enclosed by an elongated slot that allows movement of the flange member 30 to conform with patient movement during use.

Additionally, FIG. 3 illustrates the cannula 12 positioning within the inner spherical bearing element 26 when assembled. As shown, the proximal end 14 of the cannula 12 is retained along the upper connector 24 in the spherical body 54. In one embodiment, a pin 78 couples the cannula 12 to the spherical body 54, for example, via an aperture disposed in the cannula 12. However, in other embodiments, the cannula may be retained in the spherical bearing element 26 in any of a variety of suitable ways. Indeed, in some embodiments, the cannula 12, the inner spherical bearing element 26, and the upper connector 24 of the first subassembly 28 may be formed as a single integral unit.

Figure 4:
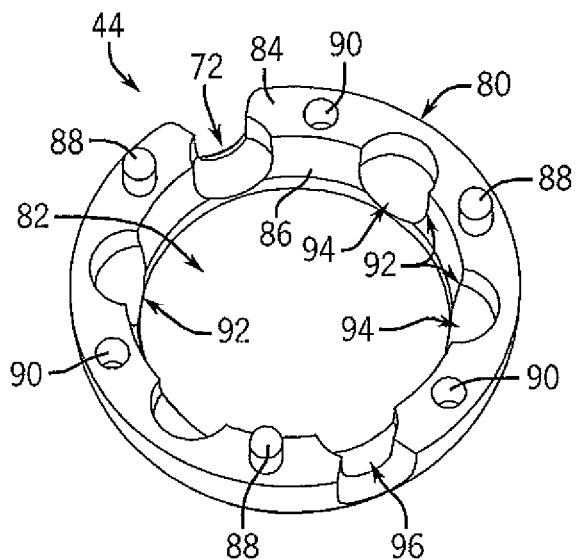
FIG. 4 is a perspective view of a boss member of the tracheostomy tube assembly embodiment of FIG. 1.

FIG. 4 is a bottom perspective view of the boss member 44 that may be a component of the outer spherical bearing member in some embodiments. As shown, the boss member 44 is substantially an annular ring 80 that defines a central aperture 82. The annular ring 80 includes a bottom surface 84 and an inner surface 86. The bottom surface 84 includes cylindrical protrusions 88 and cylindrical apertures 90 that are configured to mate with apertures and protrusions, respectively, located on the annular ring 64 of the flange member 30 to form a unified assembly. It should be noted that the illustrated cylindrical protrusion and aperture configuration is merely an example; in other embodiments, the protrusions and apertures may take on other shapes or other features may be utilized to couple the components together. For example, in one embodiment, the boss member 44 may include only apertures and the annular ring 64 may include only protrusions. Still further, in some embodiments, identifiers may be located on the protrusions 88 and/or near the apertures 90 to facilitate proper alignment with the annular ring 64 of the flange member 30.

The annular ring 80 also includes recesses 92 that are dimensioned to conform to the protrusions located on the inner spherical bearing element 26. To that end, in the illustrated embodiment, the recesses 92 form hemispherical pathways 94 that include curved portions to conform to the spherical protrusions shown in FIGS. 2 and 6. In the illustrated embodiment, the hemispherical pathways 94 of the boss member 44 are configured to align with hemispherical pathways of the flange member 30 to form a complete hemispherical pathway through which the protrusions of the inner spherical element 26 are free to move. Still further, recesses 72 and 96 are provided in the annular ring 80 to provide for coupling of the inflation line 20 and the evacuation line 74, respectively, to the cannula 12 through protrusions of the inner spherical bearing element 26.

Figure 5:
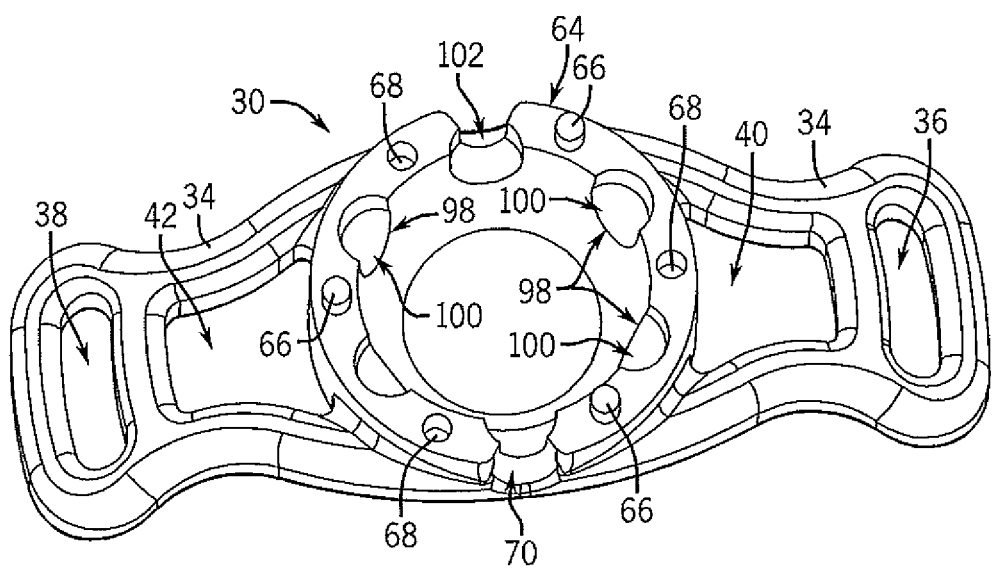
FIG. 5 is a perspective view of a flange member of the tracheostomy tube assembly of FIG. 1.

FIG. 5 is a top perspective view of the flange assembly 30 illustrating features that are complementary to those of the boss member 44 of FIG. 4 such that when the boss member 44 and the flange assembly 30 are coupled together, these components form an outer spherical bearing element 32 that encircles the inner spherical bearing element 26. To that end, the flange assembly 30 includes features disposed on the annular ring 64 that are similar to those of the boss member 44. For example, as described above, the annular ring 64 includes protrusions 66 that are configured to be received by apertures 90 of the boss member 44. The annular ring 64 also includes apertures 68 that are configured to receive the protrusions 88 of the boss member 44.

Still further, the flange assembly 30 also includes recesses 98 that form hemispherical pathways 100 with arcuate portions dimensioned to receive the spherical protrusions of the inner spherical bearing member 26. As previously mentioned, the hemispherical pathways 100 of the flange member 30 are configured to align with the hemispherical pathways 94 of the boss member 44 to form complete hemispherical pathways through which the protrusions of the inner spherical element 26 are free to move. That is, in some embodiments, the spherical protrusions disposed in the hemispherical pathways may not be configured to lock into place, but rather are free to move within the bounds defined by the hemispherical pathways in accordance with one or more external forces exerted thereon during use. In certain embodiments, if desired, one or more coatings may be applied to the hemispherical pathways to facilitate such freedom of movement and to substantially reduce friction between the protrusions and the pathways during movement. Additionally, recesses 70 and 102 are provided in the annular ring 64 to provide for coupling of the inflation line 20 and the evacuation line 74 to the cannula 12 through protrusions of the inner spherical bearing element 26. The recesses 70 and 102 of the flange member 30 are configured to align with the recesses 72 and 96 as shown in FIG. 1.

Figure 6:
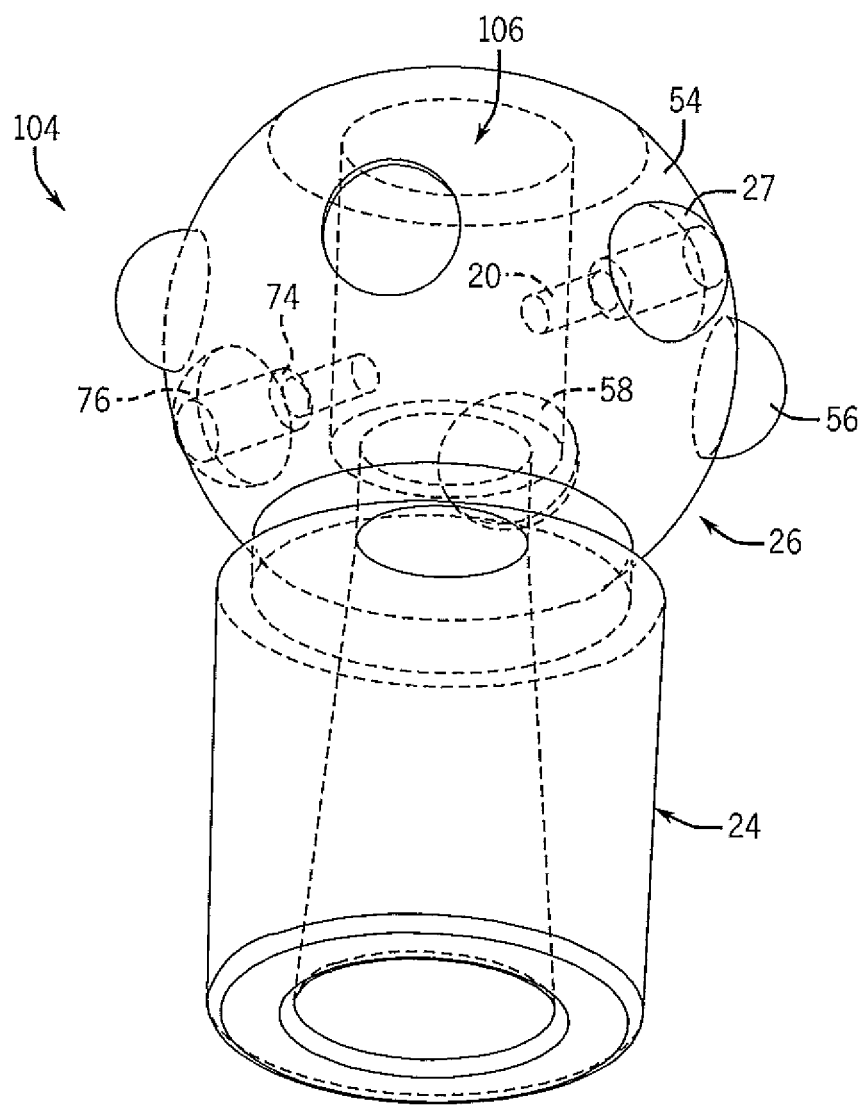
FIG. 6 is a perspective view of a connector subassembly of the embodiment of the tracheostomy tube assembly of FIG. 1.

FIG. 6 is a perspective view of a connector subassembly 104 of the embodiment of the tracheostomy tube assembly 10 illustrated in FIG. 1. As shown, the connector subassembly 104 includes the upper connector 24 coupled to the inner spherical bearing element 26. The inner spherical bearing element 26 includes the illustrated protrusions 76, 58, 56, and 27 as well as additional protrusions not shown in the illustrated view. In this embodiment, the protrusions 76, 58, 56, and 27 are generally spherical in shape, but are subject to considerable variations in size and shape in other embodiments. As before, the body 54 of the bearing element 26 is also spherical in shape and includes an aperture 106 that extends through its length to facilitate airflow through the upper connector 24 and the body 54 as well as the cannula 12 during operation. Still further, the upper connector 24 and/or the inner spherical bearing element 26 may be formed from any suitable rigid material, such as acrylonitrile butadiene styrene (ABS).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheostomy tube assembly, comprising: a first subassembly comprising a lower cannula, an upper connector, and an inner spherical bearing element disposed between the lower cannula and the upper connector and comprising at least two protrusions; a flange member comprising an outer spherical bearing element having recesses for receiving the at least two protrusions and being configured to encircle the inner spherical bearing element; and a cuff disposed on a distal end of the lower cannula and configured to inflate to seal against a patient's trachea.

2. The tracheostomy tube assembly of claim 1, wherein the at least two protrusions comprise spherically shaped protrusions, and the recesses comprise hemispherical pathways.

3. The tracheostomy tube assembly of claim 1, wherein at least one of the at least two protrusions is configured to receive an inflation line coupled to the cuff.

4. The tracheostomy tube assembly of claim 1, wherein at least one of the at least two protrusions is configured to receive an evacuation line coupled to an evacuation port disposed at a distal end of the cannula.

5. The tracheostomy tube assembly of claim 1, wherein the outer spherical bearing element comprises a two-piece assembly comprising a boss member and a flange.

6. The tracheostomy tube assembly of claim 5, wherein the boss member comprises one or more protrusions configured to be received by one or more apertures disposed in the flange.

7. The tracheostomy tube assembly of claim 5, wherein the flange comprises one or more protrusions configured to be received by one or more apertures disposed in the boss member.

8. A tracheostomy tube assembly, comprising: a cannula comprising a distal end and a proximal end, the distal end being adapted to be inserted into a patient's trachea; a connector subassembly comprising an annular connector portion coupled to a spherical portion comprising at least two spherical protrusions radially disposed about a circumference of the spherical portion, wherein the spherical portion is configured to receive and retain the proximal end of the cannula; an annular boss member comprising an annular ring defining a central aperture configured to receive the annular connector portion; and a flange member comprising at least two additional hemispherical recesses configured to align with the at least two hemispherical recesses of the annular boss member to form at least two hemispherical pathways, wherein the at least two hemispherical pathways are configured to receive the at least two spherical protrusions.

9. The tracheostomy tube assembly of claim 8, wherein the connector subassembly is made of a rigid thermoplastic material.

10. The tracheostomy tube assembly of claim 8, wherein the connector subassembly is made of acrylonitrile butadiene styrene.

11. The tracheostomy tube assembly of claim 8, wherein the flange member comprises two flanges configured to rest against a neck of a patient when the distal end of the cannula is inserted into the patient's trachea.

12. The tracheostomy tube assembly of claim 8, wherein one of the annular ring of the annular boss member and the flange member comprises at least one protrusion and the other of the annular ring and the flange member comprises an aperture configured to receive the protrusion to couple the annular boss member to the flange member.

13. The tracheostomy tube assembly of claim 8, wherein the at least two spherical protrusions are configured to move within the at least two hemispherical pathways without substantial movement of the cannula in the patient's trachea when the distal end of the cannula is inserted into the patient's trachea.

14. The tracheostomy tube assembly of claim 8, wherein the at least two spherical protrusions comprise six spherical protrusions, and the at least two hemispherical pathways comprise six hemispherical pathways.

15. A tracheostomy assembly, comprising: a first subassembly comprising a connector and a first spherical bearing element coupled to a first end of the connector, wherein the first spherical bearing element comprises six protrusions radially offset approximately 60 degrees about a circumference of the first spherical bearing element; and a flange subassembly comprising an outer spherical bearing element having hemispherical pathways for receiving and encapsulating the six protrusions and being configured to encapsulate the first spherical bearing element.

16. The tracheostomy assembly of claim 15, wherein the six protrusions comprise spherical protrusions.

17. The tracheostomy assembly of claim 15, wherein the first subassembly comprises a cannula coupled to a second end of the connector.

18. The tracheostomy assembly of claim 15, wherein two of the six protrusions disposed on opposite surfaces of the first spherical bearing element are each configured to receive one of an inflation conduit or an evacuation conduit.

* * * * *